United States Patent [19]

Taylor

[11] Patent Number: 5,326,532
[45] Date of Patent: Jul. 5, 1994

[54] APPARATUS FOR CHEMICALLY PROCESSING TOXIC MATERIALS

[75] Inventor: William R. Taylor, Dunstable, Mass.

[73] Assignee: E. I. Du Pont de Nemours and Company, Wilmington, Del.

[21] Appl. No.: 27,911

[22] Filed: Feb. 25, 1993

[51] Int. Cl.$^5$ .............. G01N 1/10; G01N 1/34
[52] U.S. Cl. .................... 422/100; 422/63;
422/71; 422/103; 422/159; 73/863.33;
73/863.85; 73/864.21; 73/61.55; 73/61.56
[58] Field of Search ............... 422/63, 71, 100, 103,
422/159; 73/863.32, 863.33, 864.21, 864.24,
863.85, 61.55, 61.56

[56] References Cited

U.S. PATENT DOCUMENTS

| | | | |
|---|---|---|---|
| 3,383,923 | 5/1968 | Conche et al. | 73/864.31 X |
| 3,743,714 | 7/1973 | Deutsch | 422/159 X |
| 3,774,035 | 11/1973 | Litt | 422/159 X |
| 3,898,044 | 8/1975 | Strecker et al. | 422/159 X |
| 3,940,995 | 3/1976 | Hawis et al. | 73/422 E X |
| 4,094,195 | 6/1978 | Friswell et al. | 73/864.21 X |
| 4,155,711 | 5/1979 | Zelagin et al. | 422/65 X |
| 4,271,127 | 6/1981 | Borner et al. | 422/159 |
| 4,280,053 | 7/1981 | Evans et al. | 422/159 X |
| 4,476,734 | 10/1984 | Banks et al. | 73/864.16 |
| 4,512,203 | 4/1985 | Calame-Lonjean et al. | 73/863.81 |
| 4,549,440 | 10/1985 | Fournier et al. | 73/863.85 |
| 4,615,226 | 10/1986 | DiNuzzo et al. | 73/864.24 X |
| 4,615,833 | 10/1986 | Kaufmann | 422/159 X |
| 4,626,414 | 12/1986 | Baatz et al. | 422/159 |
| 4,653,333 | 3/1987 | Zeh | 73/863.81 |
| 4,662,231 | 5/1987 | Schaarschmidt et al. | 73/864.31 X |
| 5,130,254 | 7/1992 | Collier et al. | 436/54 |
| 5,156,818 | 10/1992 | Manchak et al. | 422/159 |
| 5,206,346 | 4/1993 | Taylor | 422/159 X |

FOREIGN PATENT DOCUMENTS

| | | | |
|---|---|---|---|
| 0349952 | 7/1989 | European Pat. Off. | G01N 1/14 |
| 3044424A1 | 11/1980 | Fed. Rep. of Germany | G01T 7/02 |
| 2203243A | 3/1988 | United Kingdom | G01N 35/00 |

Primary Examiner—Jill A. Johnston
Assistant Examiner—Harold Y. Pyon

[57] ABSTRACT

An apparatus is provided for processing toxic materials in a safe manner. Two access ports in the apparatus are used for introducing and withdrawing the materials. In the apparatus, two valves pass the materials through a vial for mixing with a stored toxic material and a column for processing.

8 Claims, 8 Drawing Sheets

APPARATUS FOR CHEMICALLY PROCESSING TOXIC MATERIALS

FIELD OF THE INVENTION

The present invention relates to an apparatus for the preparation and processing of toxic materials and, more particularly, to an apparatus for iodinating various biological materials with radioactive iodine species.

DESCRIPTION OF THE PRIOR ART

The use of radiolabeled therapeutic and diagnostic agents has recently received renewed interest. The development of monoclonal antibodies of high affinity and specificity has encouraged the development of new agents for diagnostic and therapeutic treatment of cancer. These radiolabeled monoclonal antibodies, ligands, unsaturated fatty acids and other compounds are finding clinical applications both in vitro and in vivo. With this increased usage comes the problem of how to safely handle the materials. One is faced with the same problem when handling chemical and biological systems, i.e., to provide a safe product that is sterile and represents little danger to persons processing the materials.

Other shieldable, disposable and relatively cheap systems are reported (see for example, Weadock K. S., Anderson L. L., Kassis A. I., A simple remote system for the high-level radioiodination of monoclonal antibodies; J Nuc Med All Sci 1989;33:37–41, or James Watson S. F., Fairweather D. S., Bradwell A. R., A Shielded, Sterile Apparatus for Iodinating Proteins, Med Lab Sci 1983; 40:67–68.) but these systems are complex to use requiring manipulation of valves and positioning of needles. These systems are inherently less reliable for iodinating since the result will depend on the mechanics of vial coating and the timing of the iodination and purification reactions. These systems are also more difficult to shield than the present invention because there are multiple vials to shield (apparatus is spread out) and a lead wall is also required.

Van Loon et al., EP-349952, filed Jan. 10, 1990, discloses a pneumatic sampling device for sample extraction of radioactive fluids. This device uses a hollow needle for extracting the sample fluid from an ampoule and supplying it to a sample container via an attached fluid line and is relatively complicated in requiring moving parts and an electromagnetic actuation for selectively allowing reduced pressure to the needle.

H. Zeh, U.S. Pat. No. 4,653,333, issued Mar. 31, 1987, discloses an apparatus for filling bottles with samples of toxic and/or radioactive fluids. An essential feature of the Zeh apparatus is the ability to provide a means to present a sample bottle, fill it and remove it from within a shielded environment. Bottles are supplied to, and taken from, the fill location via pneumatic bottle transport line control of which is effected by rotation of an axial shaft. The apparatus requires that the bottle supply and fill needle be coaxial. The subject invention is simple and does not require transfer bottles to/from the apparatus, coaxial needles, or a rotatable seal within the system.

SUMMARY OF THE INVENTION

The apparatus of this invention reduces many of the disadvantages of these prior art apparatus for processing toxic fluids. The term toxic is used to apply to fluids which represent chemical, biological, or radiological hazards to the operator. The apparatus of this invention is operative to effect a chemical change on a fluid initially within the system, added to the system, or pooled within the system by sequential addition. The apparatus causes a fluid to be processed by a simple mechanism to pass through a chemical reaction, ion exchange, or purification column, which is integrated into the flow path of the fluid. The apparatus protects the operator from toxicological hazards and simply and automatically delivers the chemically modified fluid to a receiving well or vial and can be maintained in a sterile condition.

This invention provides an apparatus for passing fluid through a processing column for effecting chemical change in the fluid, the fluid being disposed in a vial in a closed container, the container having a top and first and second access ports, said apparatus comprising a needle assembly having first, second, and third needles, a plunger, mounting the needle assembly, disposed in and extending through the top of the container and being actuatable from outside the container to introduce the needle assembly into the vial, the processing column mounted by the actuator, the first port and first needle being interconnected, and valve means disposed in the container, actuatable from outside the container, for connecting the second access port alternatively (a) to the second needle and (b) to the third needle through the processing column.

In an alternative embodiment of the invention, the apparatus includes radioactive materials positioned in the vial and a shield for the radioactive materials. The shield is positioned in the container about the periphery of the vial. Preferably, the processing column is positioned in the plunger and the third needle extends farther than the first and second needles into the vial when the plunger is actuated. Also, preferably, the first needle extends further than the second needle into the vial when the plunger is actuated.

In a further preferred embodiment of the invention the sleeve is positioned in the container engaging the vial and the plunger is slideably positioned in sleeve. Detents may be provided to control the movement of the plunger.

The apparatus is seen to be entirely self contained and provides a barrier between user and the materials being manipulated within the system. Fluids being manipulated can be thus maintained in a sterile condition within the system. Conversely the user can be protected from chemical, biological or radiation hazards associated with the fluids being manipulated within the apparatus by virtue of the containment provided.

In a typical application of the apparatus, the user will receive the apparatus prefilled with radioactive iodine. The user can radiolabel and purify the biomolecule of his/her choice without ever handling the radioactivity itself. No radioactive waste is generated and the system can be returned to the vendor to be reused.

BRIEF DESCRIPTION OF THE DRAWINGS

The invention may be more fully understood from the following detailed description thereof taken in connection with the accompanying drawings which form a part of this application and in which.

DETAILED DESCRIPTION OF THE PREFERRED EMBODIMENT

Figure 1:
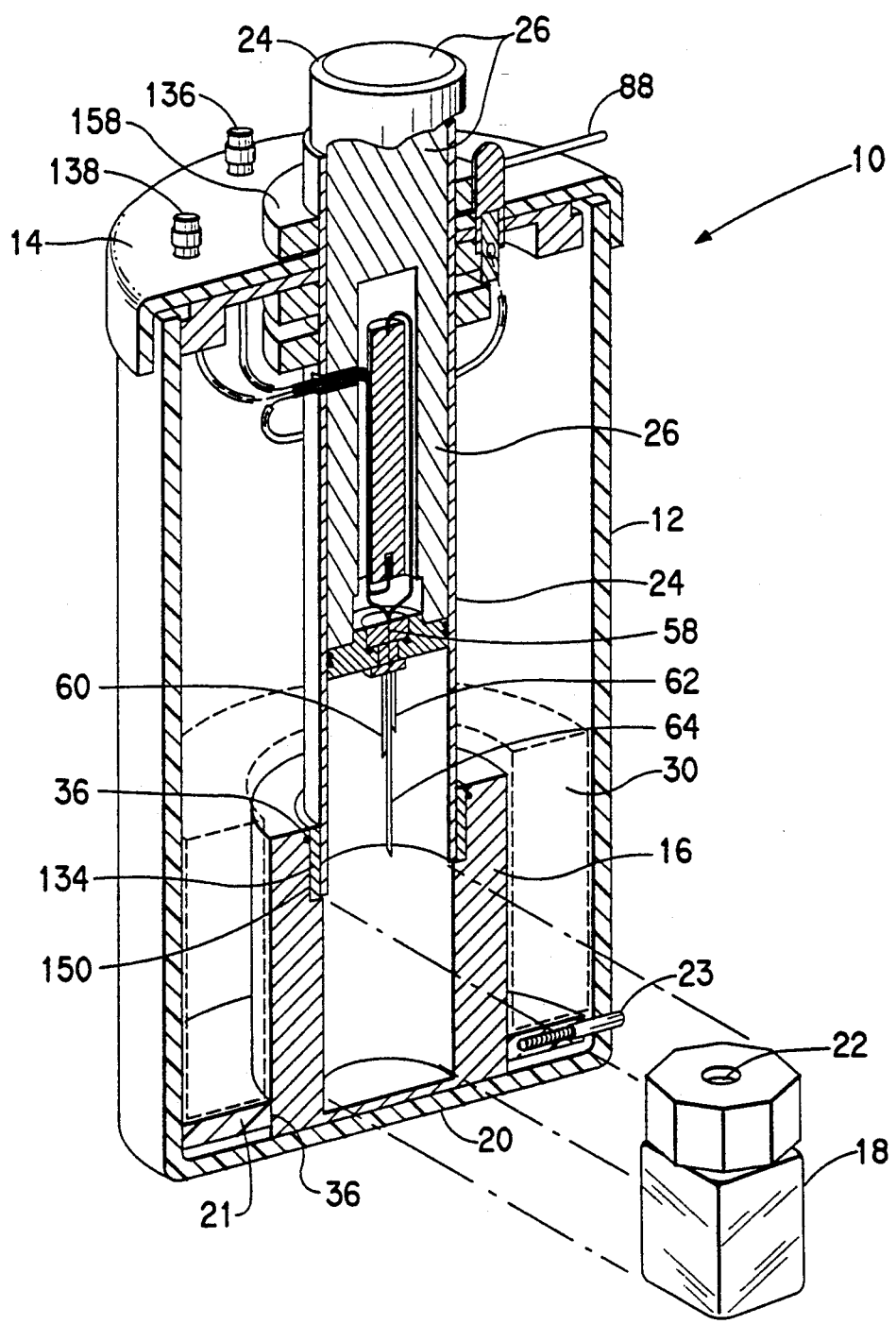
FIG. 1 is a pictorial view of the container apparatus of this invention cut away to reveal the internal features of the apparatus.

The apparatus of this invention may be seen with particular reference to FIGS. 1 through 6. This apparatus consititutes a sealed system in use and an infusion pump may be connected to the IV sites 136 and 138. These IV sites may be no more than an access port closed by a septum providing access to the interior of a container 12 which together with cover 14 provides the chemical processing apparatus 10 of this invention. By propelling downwardly the plunger 26, which is sealed against the outside of the container 12, drives a needle set assembly 58 through the septum seal 22 of a vial, typically a NENSURE TM described in U.S. Pat. No. 4,788,438. The NENSURE TM vial is positioned on the bottom surface of the container 12 and positioned by a vial holder 16 which is in turn positioned by a centering collar 21 secured by a set screw 23. The vial holder 16 is positioned by the central bore 36 of the centering collar 21.

A reaction column 38 is integrated into the needle set assembly 58 so that it is in the fluid flow path of the needle set assembly 58 as will be described. Activation of the infaston pump drives fluids through the system. Positioning a three way step cock valve 100 allows the operator to introduce fluids from an external source to the vial 18 and/or to direct a fluid from the vial 18 through the reaction column 38 to affect a chemical change. The reaction column 38 may be a chemical reaction column, an ion exchange column or purification column or similar column or a combination thereof. For the sake of simplicity, this invention will be described as if in the environment in which the chemical reaction column is a radioiodination column of the type described in EPO published application No. 91120712/4.

As is described in that application, the column has an inlet end and an outlet end and is packed with sequential stages of beads coated with an oxidizing reagent for coupling the radioisotopes to the biomolecule. The column includes an aion exchange resin and a material for trapping elemental radioisotope. A mixture of the radioisotope and a solution of the material to be labelled are flowed through the column and the purified product collected at the effluent end of the column. In this instance, the radioisotope is shipped and provided in the vial 18. The radiolabeling reaction (incorporation of radiolabeled into the functional material) and a purification reaction (removal of unincorporated radiolabels from the radiolabeled material) occur as a reaction mixture flows through the column. In addition, all unincorporated radiolabel is contained and trapped within the column, thus, reducing the quantity of radioactive waste generated and eliminating the end user having a need to handle this waste.

Figure 2:
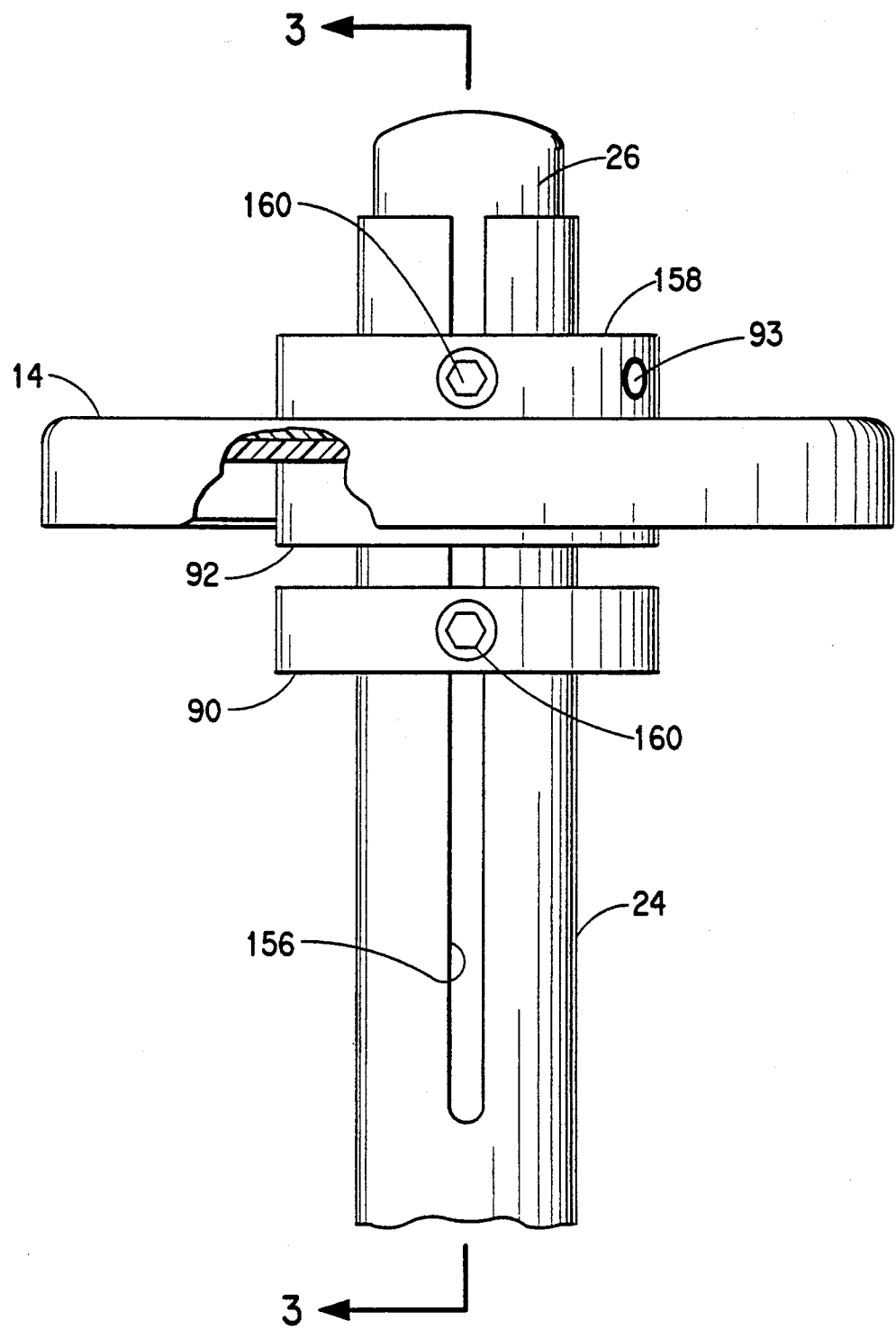
FIG. 2 is a side elevation view of the cover assembly partially cut away.
Figure 3:
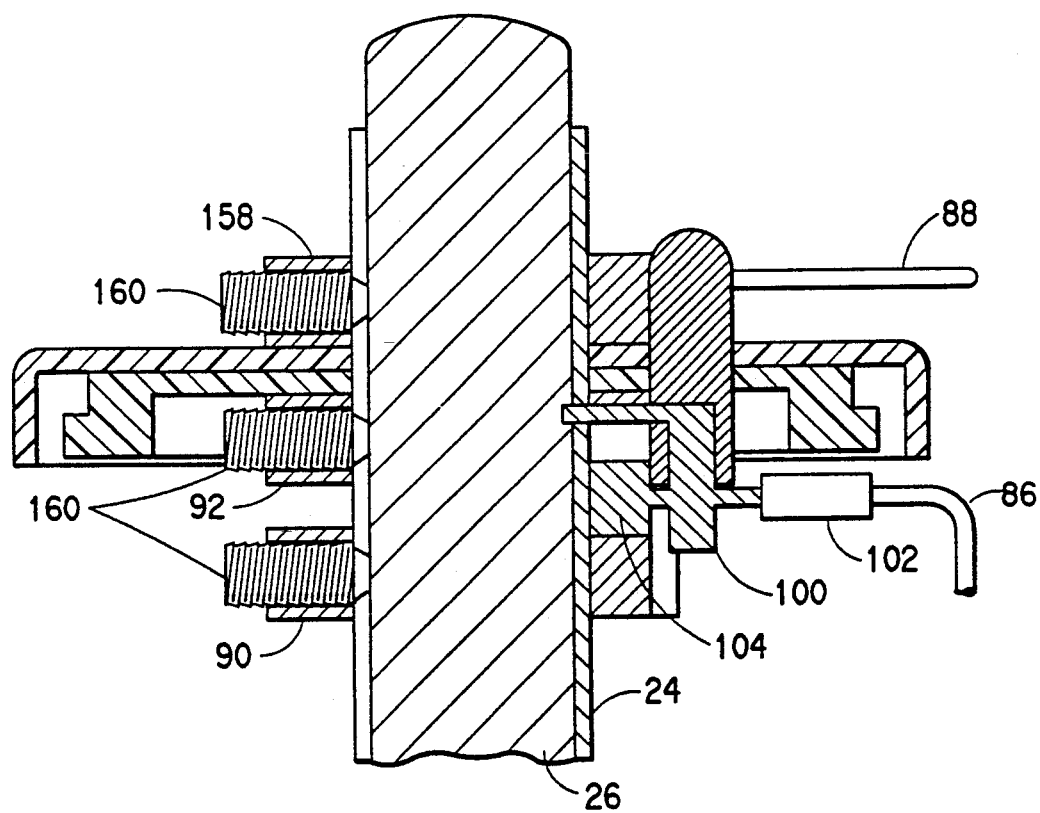
FIG. 3 is a cross section view taken along the section line 3—3 of FIG. 2.

The apparatus of this invention is thus seen to include a chemical processing apparatus 10 which comprises essentially a container 12 and a cover 14. A plunger 26 is slideably positioned within a plunger sleeve 24 which extends through the cover 14 and positioned by a retaining ring 158 and set screw 93 (FIG. 2). The upper end of the plunger sleeve 24 is slotted 156. Set screws 160 and the retaining ring 158 and clamping devices 90 and 92 are positioned into the slot 156 for maintaining its degree of tightness on the plunger.

The lower end of a plunger sleeve 24 engages the vial 18 and is aligned therewith by a sleeve collar 34 positioned within a counter bore 150 in the vial holder 16 and O-ring 36 is positioned in a grove (not shown) to prevent leakage. Ball plunger detents 78 (FIG. 4) mounted on the plunger 26 act in combination with positioning holes (not shown) and the plunger sleeve 24 to define either of two vertical positions of the plunger 26 and in turn the positions of the needles 60, 62, and 64. As may be seen, the needle 62 is shortest, the needle 60 is longest, such that when the plunger is actuated it will contact the bottom of the vial 18, and finally the first needle 60 is in an intermediate position. The term "needle" as used herein is descriptive of a hollow tube or syringe-like needle. When the plunger 26 is fully extended, the needle set assembly 58 is sufficiently downwardly moved such that the hex nut 44 (as will be described) fully engages the top of the vial 18 (septum seal 22) as the third needle 64 reaches the bottom inside of the vial 18.

A guide pin 74 on the plunger 26 is registered in a longitudinal slot 156 formed in the plunger sleeve 24 to maintain the respective radial positions of the plunger 26 and the plunger sleeve 24. The slot 156 also provides a raceway within which the needle ends can travel during transition of the plunger 26 from the retracted to the extended positions.

Figure 7:
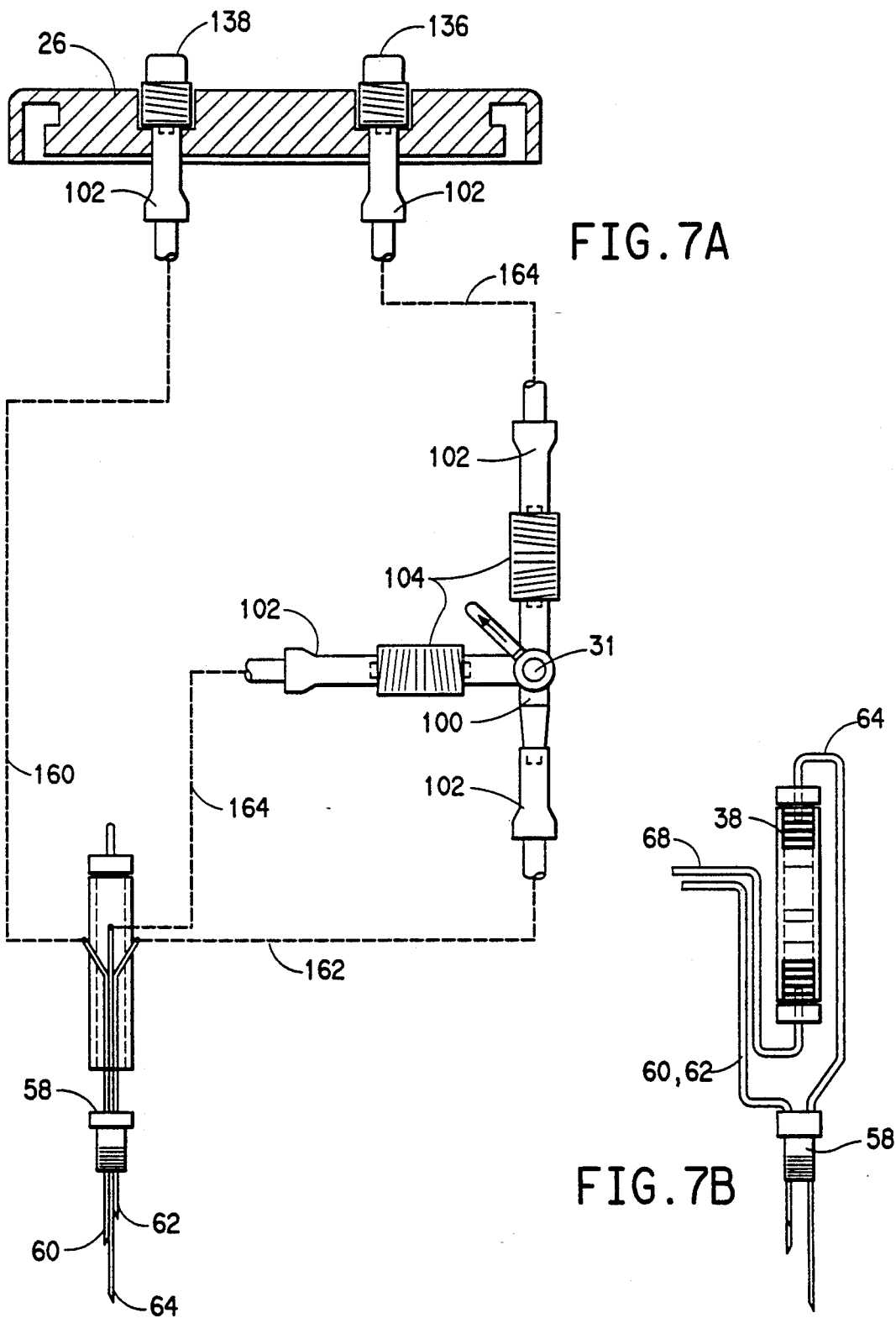
FIG. 7A is a schematic diagram depicting the fluid connections between the cover assembly, the three-way valve and the needle set assembly.
FIG. 7B is a schematic diagram depicting a portion of FIG. 7A comprising the processing column.

The lower end (in the drawing) of the plunger 26 contains a central bore 76 (FIG. 4) to receive a column 38 and connecting tubing 64, 68 (FIG. 7B). The central bore 76 is notched at 20 to allow the connecting tubing 60, 62, 64 from the needles to pass through the side wall of the plunger 26 and through the slot 156. The outer surface of the plunger 26 is longitudinally grooved continuously to the notch 20 to define a longitudinal groove 72 to allow recession of the needle connecting tubing 60, 62 and 68 below the radial circumference of the plunger 26. The central bore 76 threadly receives a cylindrical plunger endcap 42 containing two O-ring grooves 40 in the outer radial surface to receive O-rings 56. The plunger endcap 42 is provided with a central through bore 48 and a counter bore 52 to receive the vial needles 60, 62, and 64. The counter bore 52 additionally provides a smooth horizontal sealing surface to receive an O-ring 50 that makes and air tight seal with the vial needle set assembly 58. The two O-rings 56 make an airtight seal with the inner surface of the plunger sleeve 24. A hex nut 44 secures the vial needle set assembly 58 to the plunger endcap 42 and allows compression of the O-ring 50.

Figure 4:
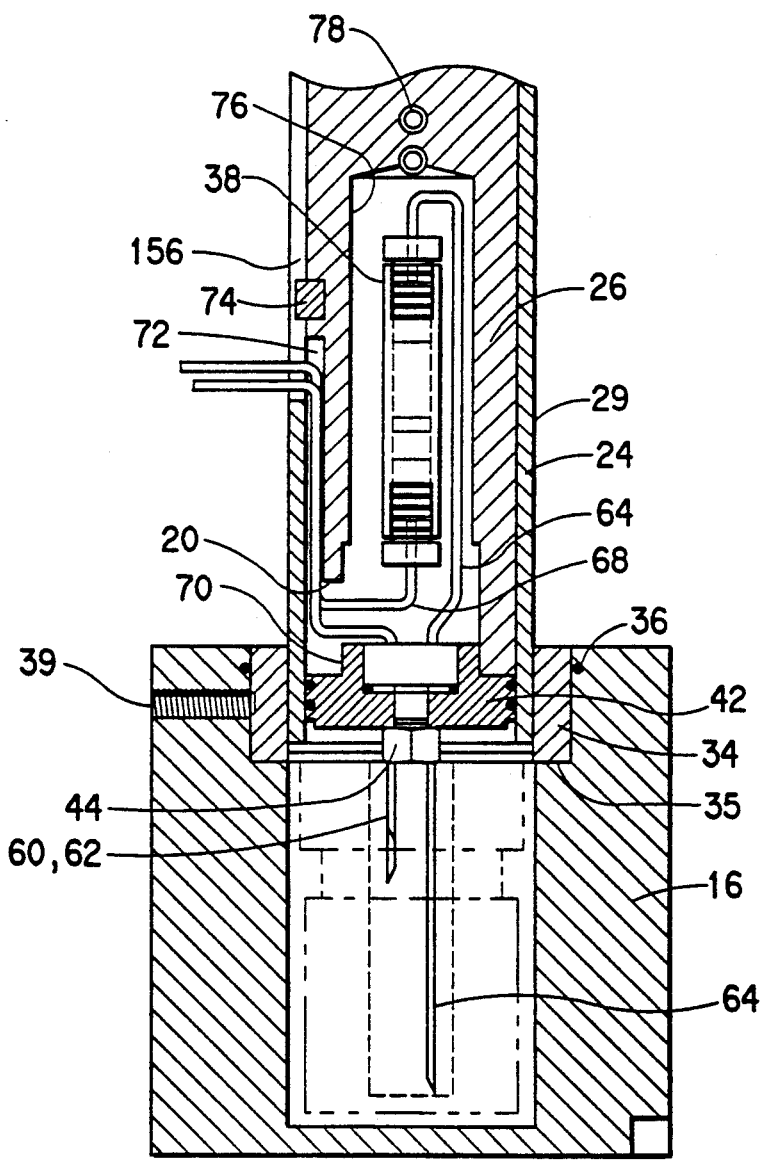
FIG. 4 is a cross sectional elevation view of the vial holder assembly of this invention depicting the plunger in an activated condition.
Figure 5:
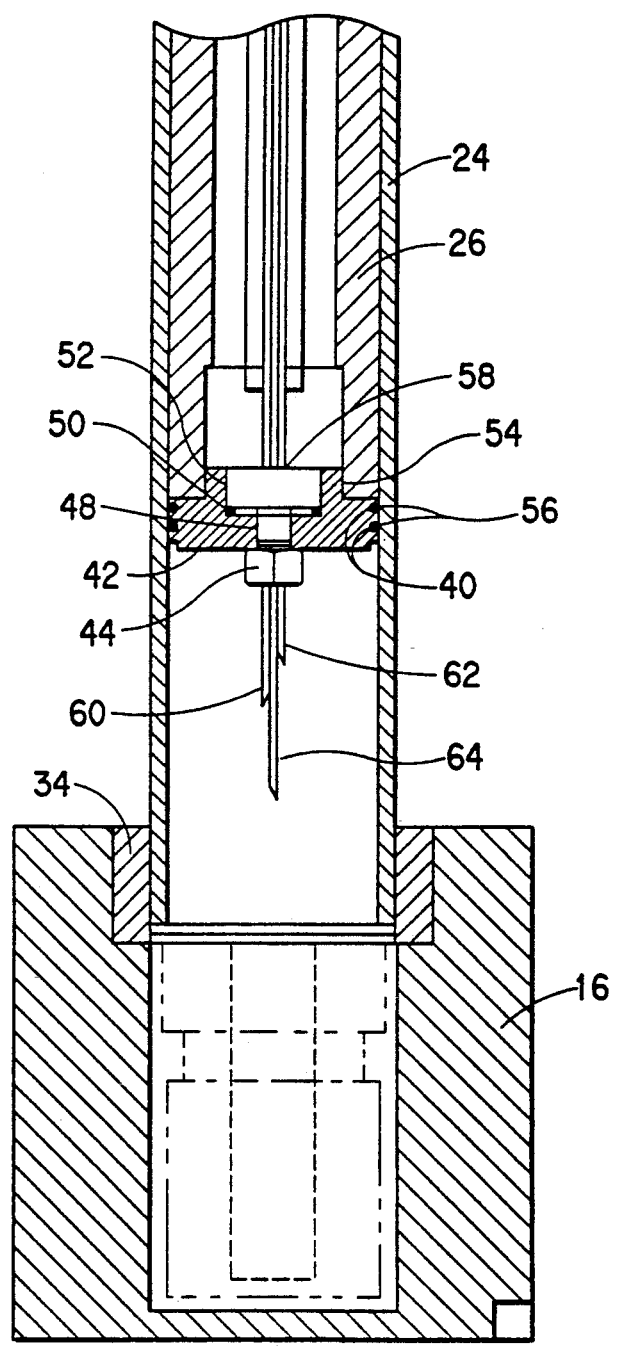
FIG. 5 is a cross sectional elevation view of the vial holder assembly of this invention with the plunger in an unactivated position.
Figure 6:
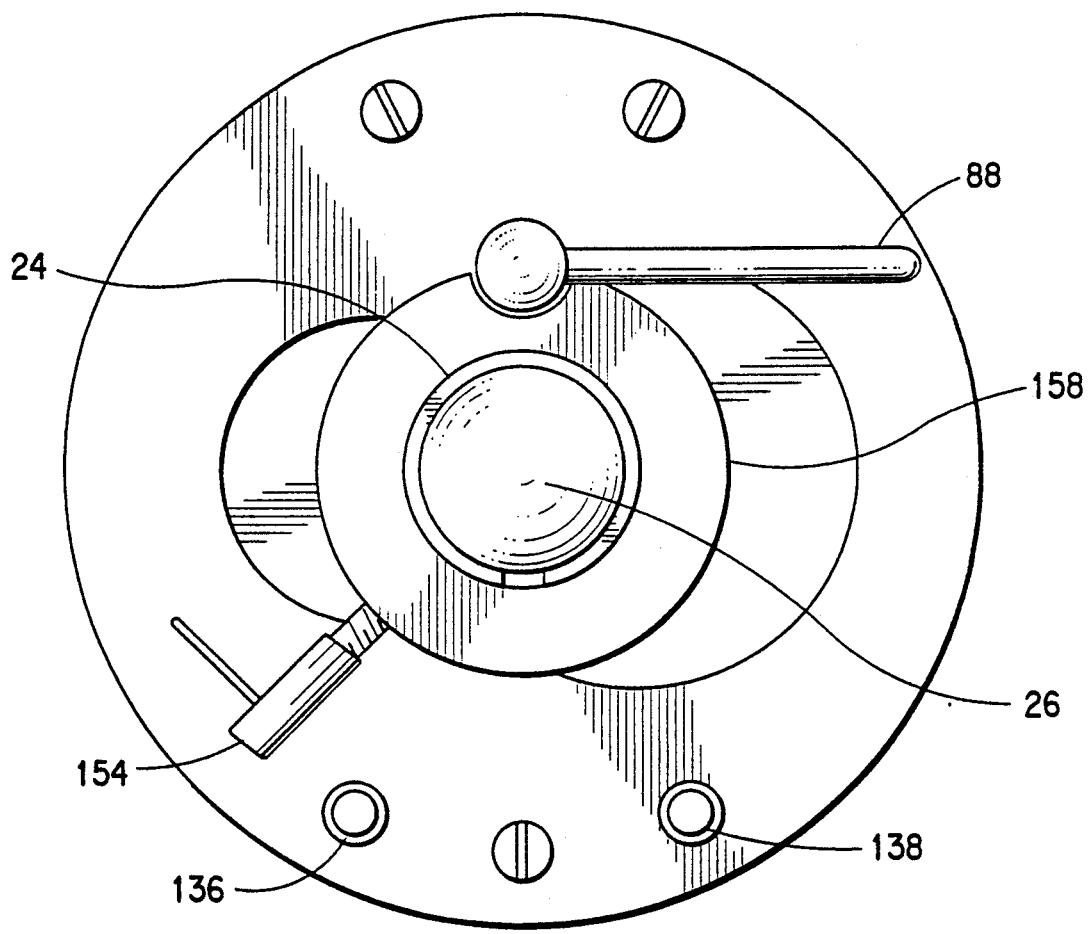
FIG. 6 is a plan view of the cover of the container.

A collar 34 is affixed to the outside lower end of the plunger guide sleeve 24. As the plunger guide sleeve 24 and collar 34 are received by the vial holder 16, a groove (not shown) in the outer radial surface of the lower end of the collar 34 accepts the ball portions of three ball plungers 39 mounted through the sidewall by the counter bore 150 of the vial holder 16 (FIGS. 1 and 4). This brings the plunger sleeve 24 and collar 34 into closely abutting engagement with the stopping surface 35 of the vial holder 16 and engages the O-ring 36 in a compression fit with the outer radial surface of the collar 34. The ball plungers 39 retain the plunger sleeve 24 to the vial holder 16 while simultaneously imparting a downward force at the interface.

A two-piece clamping device in the form of rings 90 and 92 (FIG. 2) is provided to secure a three-way stop cock valve 100 (FIGS. 3 and 7A) for directing fluid flow through the apparatus. Each clamping piece 90 and 92 has a central bore extending through the piece allowing the clamps 90 and 92 to be positioned around the plunger sleeve 24. The upper planar surface of the valve clamp 90 and the lower planar surface of the valve clamp 92 are relieved to accept a three-way stop cock valve 100 fitted with double male luhr adaptors 104. The clamping pieces 90 and 92 are secured to the plunger guide with set screws 93 (FIG. 2). The clamping pieces 90 and 92 additionally are provided with set screws 160 that engage the slot 156 in the plunger sleeve 24, thus maintaining the circumferential dimension of the plunger sleeve 24 against the compressive force of the mounting set screws 93. A valve handle 88 extends through the cover 14 to engage the three-way stop cock valve 100.

A retaining ring 158 is provided with a central bore to allow positioning around the plunger sleeve 24 on top of the cover 14. The retaining ring 158 is secured to the plunger guide with set screws 93. Set screw 160 engages the slot 156 in the plunger sleeve 24 to maintain the circumferential dimension of the plunger sleeve 24 against the compressive force of the mounting screw 95. The retaining ring 158 is notched to provide clearance for the valve handle 10 to engage the three-way stop cock valve 100. The retaining ring is provided with a spring plunger 154 which engages either of two holes (not shown) in the plunger 26. Engagement of the spring plunger 154 with the holes in the plunger 26 thus locks the plunger 26 into either of two fixed vertical positions. In the retracted position, the needles 60, 62, and 64 are enclosed within the plunger sleeve 24 above the vial. In the extended position (FIG. 5), the needles 60, 62 and 64 are fully engaged to the vial with the hex nut 44 contacting the top of the vial 18 and the long needle 64 is at the bottom inside of the vial.

As can be seen most clearly in FIGS. 7A and 7B, the first needle 60 is connected to the vent/rinse IV site 138 using connector sleeves 102 and silicone tubing 160. The second needle 62 is connected using silicone sleeves 102 and silicone tubing to the three-way valve 100. Finally the third needle 64 using a silicone sleeve 102 to the double male Luhr lock adapter 104 and hence to the three-way valve 100. The top end in the drawing of the three-way valve is connected through a silicone sleeve 102 and Luhr lock adapter 104 and silicone tubing 160 to a vacuum/product IV site 136.

Operation

Figure 8:
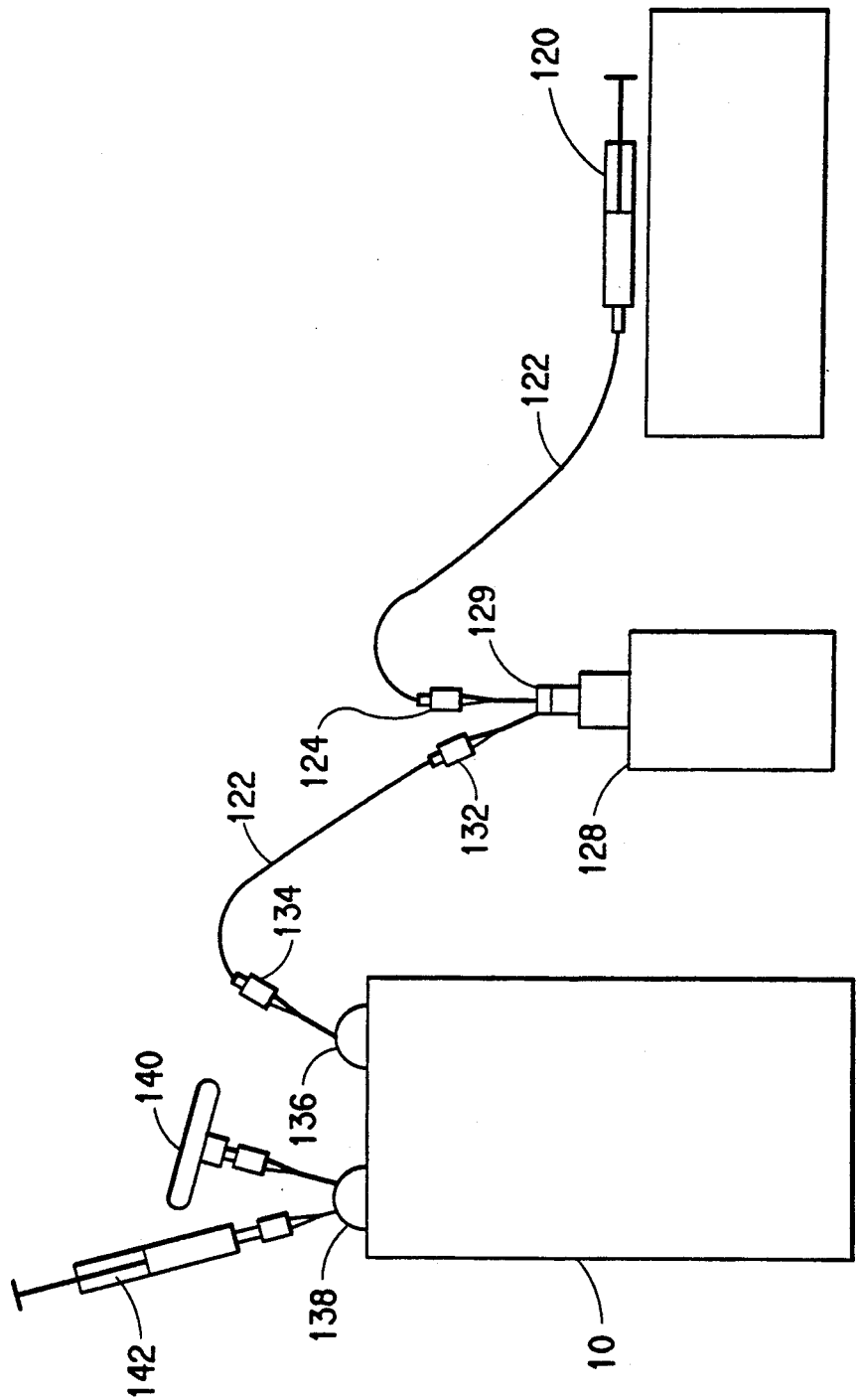
FIG. 8 is a block diagram of the apparatus of this invention in use in a typical application.

The operation of the system shown in the Figures may be understood by reference to FIG. 8 taken in conjunction with FIGS. 1 through 7A and 7B. The needles 60, 62, 64 initially occupy a retracted position with respect to the plunger sleeve 24 as seen most clearly in FIG. 5, and the spring plunger 154 (FIG. 6) is engaged to prevent movement of the needles 60, 62, 64 during the shipment of the apparatus. In the retracted position, the lower ends of the needles lies above the septum seal 22 and is enclosed by the plunger/sleeve 26–24. Typically the vial 18, in the illustrative example, contains radioactive iodine. The needles 60, 62 and 64 are fitted with an iodination reaction column 38, of the type described previously, for the purpose of iodination and purification of a monoclonal antibody.

An infusion pump (FIG. 8), as denoted by syringe-type element 120, and a receiving vial 128 for the iodinated product are connected to the apparatus through silicone tubing 122 and connected into the infusion pump 120. The free end of the silicone tubing 122 is connected to a sterile needle 124 using double male Luhr lock adaptor. The sterile needle is inserted into the top port of a needle guide in the receiving vial 128. A second length of silicone tubing 122 is connected at both ends to sterile needles 132, 134 which are inserted into the vacuum/product and the side port 132 of the needle guide 129. Disengagement of the spring plunger 154 (FIG. 6) allows the extension of the needles 60, 62 and 64 in a downward direction by the application of pressure on the top of plunger 26. Extension of the needles 60–64 causes the vial septum to be pierced and extension continues until limited by contact by the hex nut 44 on the top of septum 22. At this point the third needle 64 will be at the bottom of the vial 18 and the detents 78 engage the positioning holes in the ball plunger sleeve 24 to prevent retractive movement of the plunger 26 due to the counter force exerted by the septum seal 22 on the needles 60–64.

An appropriate monoclonal antibody is introduced into the vial by piercing the vent/rinse site 138 with a needle of syringe 142 containing the antibody in buffer solution, turning the valve handle 88 to the vent/rinse position and engaging the infusion pump 120 suction. Addition of the antibody at a flow rate of 10 mL/min. to the vial 18 will insure complete mixing of the antibody with the radioactivity.

To initiate flow of monoclonal antibody iodine solution from the vial 18 through the reaction column 38 and then to the receiving vial 128, the valve handle 88 is placed in the vacuum/product out position. The syringe 142 previously containing the antibody buffer solution is removed from the vent/rinse IV site 138 and is replaced with a sterile 0.2 micron venting filter 140 fitted with a sterile needle and the pump 120 is engaged to create a suction at a flow rate of 1 mL/min. The antibody/iodine pool flows from the vial 18 to the reaction column 38 where the antibody is labeled and purified. The flow path continues through the vacuum/product out IV 136 site and into the product receiving vial 128. The product is now ready for use with no further preparation required.

The needle connection to the IV site 136 of the system removed, the spring plunger 154 is engaged, locking the plunger 26 in the down position. The vial needles are thus fully engaged to the vial maintaining the sealed system. The system is then returned to the vendor for reuse. The many advantageous set forth hereinbefore is to the invention thus realized.

Alternative Embodiments

The apparatus for chemically processing toxic materials may be applied to the radiolabeling of antibodies with isotopes other than iodeine as, for example, in the labeling of IgG with copper-64 or copper-57. For this purpose, a well known method for the attachment of bis-TSC bifunctional cheleates to the antibody of choice is utilized. For example, the IgG of interest may be labeled with the bis-TSC chelate, 1-(p-Carboxypropylphenyl)-1,2-propandione bis 4-methyl-3-thiosemicarbazone, and the ligand attached antibody obtained as a lyophilized solid. The apparatus of the invention is received from the vendor prefilled with copper-67 chloride for example and is fitted with a Sephadex G-25 gel filtration column to effect the required purification of the product.

The user dissolves the antibody complex in a buffer solution and injects the solution into the system as previously described. The radiolabeling reaction is allowed to proceed in the vial. The reaction solution is then pumped through the purification column where unreacted Cu-67, ligand and reaction by-products are removed from the reaction mixture. Purified, radiolabeled product is delivered to the receiving vial ready for use.

The synthesis of Br-82 and Br-77 radiolabeled 17a-bromovinylestradiol, a steroid analog utilized in imaging human mammary carcinoma, can be effectively and safely accomplished using the apparatus. The chemical reaction involves the radiobromodestannylation of 17A-E-tri-n-butylstannylvinylestradiol initiated by the oxidation of radiobromide on the previously described iodination reaction column. The apparatus of the invention is received from the vendor containing a vial prefilled with $Na^{82}Br$ in methanol and fitted with the previously described iodination column.

17a-E-tri-n-butylstannylvinylestradiol methanol solution is injected into the vial containing the radiolabel. The reactant then would flow from the vial through the reaction column where the steroid is labeled and purified. The flow path continues through the vacuum/product out IV site, and into the product receiving vial. The product is now ready for use with no further preparation required.

The apparatus can be effectively utilized in synthesizing 99 m Tc complex formation agents as, for example, in the case of the synthesis of the hepatobiliary imaging agent 99 m Tc-Iodofenin, 3-iodo-2,4,6-trimethylphenyl-carbamoylmethyl-iminodiacetic acid-99 mTc. In this application the reaction column is filled sequentially with an anion resin for trapping unreacted radiolabel and an activated aluminum oxide layer upon which radioactive 99 Mo has been bound by an ion exchange mechanism. The 99 Mo decays to 99 mTc and thus this layer acts as a 99 mTc isotope generator.

A buffer solution pH 5-6 containing Iodofenin ca 40 mg and stannous chloride 10 mg is drawn into the vial through the vent/rinse IV site. A saline solution is then drawn into the vial through the product out IV site causing elution of 99 mTc from the aluminum oxide layer into the reaction mixture in the vial. 99 mTc labeling of Iodofenin follows the chemical reduction of 99 mTcO4 by the stannous ion. Reactants are allowed to react in the vial for 15 min. after which they are drawn back through the reaction column where unreacted 99 mTc is removed on the anion exchange layer of the reaction column through the vacuum/product out IV site, and into the product receiving vial. The product is now ready for use with no further preparation required.

The apparatus of the invention is equally well suited for removal of toxic materials from solutions as, for example, in the removal of highly toxic Thallium ions produced as a reaction byproduct in the synthesis of cyclopentadienyl iron. The synthesis requires the sequential addition of an alcoholic solution of ferric chloride followed by a solution of cyclopentadienyl thallium in ethanol to the reaction vial contained within the apparatus, where the reaction is allowed to proceed ca 30 minutes. The chemical reaction proceeds to give cyclopentadienyl iron as product with highly toxic thallous ion as byproduct. The reaction is then drawn through the reaction column which is fixed into the flow path. In this case the reaction column is comprised of purified aluminum wool packed in a glass column which serves to completely remove thallous ion from the product solution, leaving it deposited on the aluminum as a solid mass. The mechanism of thallous removal depends on the reductive effect aluminum exhibits toward thallous ion, thus causing thallium to chemically plate onto the aluminum surface. The cyclopentadienyl iron product is thus detoxifyed without the requirement of direct handling.

In a similar manner, the highly toxic and mutagenic agent ethidium bromide (3,8-diammino-5-ethyl-6-phenylphenanthridinium bromide) utilized for the fluorescent labeling of microparticles may be removed from this reaction product mixture using the apparatus of this invention. In this case the reaction products are drawn from the vial through a reaction column containing a hydrophobic polymer resin, for example, polyvinylidenedifluoride upon which the mutagen is absorbed.

The apparatus may be equally well applied in the field of boiotechnology as a convenient method for endotoxin removal from biological samples where the maintenance of sterility can be important. As an example, a solution of the bioactive peptide Human Transforming Growth Factor (TGF-X) may be cleansed of endotoxin contaminants while maintaining sterility utilizing the apparatus. In this case, the peptide is introduced to the vial and drawn through a reaction column packed with a polystyrene resin containing surface bound Polymixim. Endotoxin contaminant is bound to the polymixin ligand and the TGF-X is delivered to the vial as a sterile, pyrogen-free solution.

What is claimed is:

1. Apparatus for passing a fluid through a processing column for effecting a chemical change in the fluid, the fluid being disposed in a vial having a septum seal capable of being pierced, said apparatus comprising:

a closed container having a first access port, a second access port and a bore, the vial being positioned in the bore;

a needle assembly having first, second, and third needles, the first needle being connected to the first access port, the third needle being connected to one end of the processing column;

a plunger, mounting the needle assembly, the plunger located within the bore in the container and containing the processing column, the plunger being disposed in and extending through the top of the container and being actuatable from outside the container to introduce the needle assembly into the vial through the septum seal; and valve means disposed in the container, actuatable from outside the container, for selectively connecting the second access port alternatively to the second needle or to an opposite end of the processing column.

2. The apparatus set forth in claim 1 further including radioactive materials positioned in the vial and a shield for radioactive materials positioned in the container about a portion of the vial.

3. The apparatus set forth in claim 1 wherein the processing column is positioned in the plunger.

4. The apparatus set forth in claim 1 wherein the third needle extends farther than the first and second needles into the vial when the plunger is activated.

5. The apparatus set forth in claim 4 wherein the first needle extends farther than the second needle into the vial when the plunger is activated.

6. The apparatus of claim 5 wherein a sleeve is positioned in the container engaging the vial, the plunger being slideably positioned in the sleeve.

7. The apparatus of claim 6 wherein the plunger and sleeve have a pair of detents cooperating to position the plunger in either an actuated or an unactuated position.

8. The apparatus of claim 7 which includes a seal between the plunger and sleeve, thereby to prevent the escape of toxic material from the vial.

* * * * *